United States Patent [19]
Reeve

[11] Patent Number: 5,681,946
[45] Date of Patent: *Oct. 28, 1997

[54] PRECIPITATING POLYMERS

[75] Inventor: Michael Alan Reeve, Henley-on-Thames, Great Britain

[73] Assignee: Amersham International plc, Buckinghamshire, United Kingdom

[*] Notice: The term of this patent shall not extend beyond the expiration date of Pat. No. 5,523,231.

[21] Appl. No.: 627,097

[22] Filed: Apr. 3, 1996

Related U.S. Application Data

[62] Division of Ser. No. 253,212, Jun. 2, 1994, Pat. No. 5,523,231, which is a continuation of Ser. No. 855,036, filed as PCT/GB91/00212, Feb. 13, 1991.

[30] Foreign Application Priority Data

Feb. 13, 1990 [GB] United Kingdom .................. 9003253

[51] Int. Cl.$^6$ ..................................................... C07H 21/00
[52] U.S. Cl. ..................... 536/25.4; 252/62.54; 435/270
[58] Field of Search ................... 536/25.4; 252/62.54; 435/270

[56] References Cited

U.S. PATENT DOCUMENTS

| | | | |
|---|---|---|---|
| Re. 35,340 | 10/1996 | Ichitsuka et al. | 210/198.2 |
| 3,470,057 | 9/1969 | Warren et al. | 195/1.5 |
| 4,001,197 | 1/1977 | Mitchell et al. | 260/112 |
| 4,672,040 | 6/1987 | Josephson | 436/526 |
| 4,710,472 | 12/1987 | Saur | 435/287 |
| 5,091,206 | 2/1992 | Wang et al. | 427/2 |
| 5,108,933 | 4/1992 | Liberti et al. | 436/501 |
| 5,422,279 | 6/1995 | Lawlor et al. | 436/17 |
| 5,441,635 | 8/1995 | Ichitsuka et al. | 210/198.2 |
| 5,484,701 | 1/1996 | Cocuzza et al. | 435/6 |
| 5,508,164 | 4/1996 | Kausch et al. | 435/6 |
| 5,512,439 | 4/1996 | Homes et al. | 435/6 |
| 5,523,231 | 6/1996 | Reeve | 435/270 |

FOREIGN PATENT DOCUMENTS

| | | |
|---|---|---|
| 0686243 | 2/1967 | Belgium . |
| 0162819 | 11/1985 | European Pat. Off. . |
| 0281390 | 9/1988 | European Pat. Off. . |
| 40408934 | 3/1992 | Japan . |
| 8401503 | 4/1984 | WIPO . |

OTHER PUBLICATIONS

Flygare et al., "Magnetic Aqueous Two-phase Separation in Preparative Applications," *Enzyme Microb. Biotech.*, 12(2), 95–103 (1990); Chem. Abstr., 112, p. 606, Abstr. No. 96880s (1990); only Abstract supplied.

Bitton et al., "Removal of *Escherichia coli* Bacteriophage T7 by Magnetic Filtration," *Water Res.*, 8(8), 549–551 (1974); Chem. Abstr., 82, p. 278, Abstr. No. 115,953y (1974); only Abstract supplied.

Warren, "New Purification Procedure for Biological Vaccines (Adsorption on Magnetic Iron Oxides)," *Immunization Jap. Encephalitis Conf.*, Hammon (ed.), Williams & Wilkins, Baltimore, MD, 1971, pp. 152–154; Chem. Abstr., 77, p. 308, Abstr. No. 92767w (1972); only Abstract supplied.

Munro et al., "Magnetic Seeding to Aid Recovery of Biological Precipitates," *Biotechnol. Letters*, 3(6), 297–302 (1981); Chem. Abstr., 95, pp. 394–395, Abstr. No. 76474q (1981); both Abstract and publication supplied.

*Primary Examiner*—John Kight
*Assistant Examiner*—L. Eric Crane
*Attorney, Agent, or Firm*—Wenderoth, Lind & Ponack

[57] ABSTRACT

A method of recovering a biopolymer from solution involves the use of magnetically attractable beads which do not specifically bind the polymer. The beads are suspended in the solution. Then the polymer is precipitated out of solution and becomes non-specifically associated with the beads. When the beads are magnetically drawn down, the polymer is drawn down with them. The polymer can subsequently be resolubilized and separated from the beads.

8 Claims, 4 Drawing Sheets

PRECIPITATING POLYMERS

This is a divisional application of Ser. No. 08/253,212, filed Jun. 2, 1994, now U.S. Pat. No. 5,523,231, which is a continuation of now abandoned application Ser. No. 07/855,036, filed May 1, 1992, which is the U.S. national stage of PCT/GB91/00212, filed Feb. 13, 1991.

I. BACKGROUND OF THE INVENTION

Many techniques in Molecular Biology, Biochemistry and Chemistry rely upon the process of precipitation. There are two types of precipitation.

In the first type of precipitation, the components from a complex solution that are not of interest are selectively precipitated. The precipitate and supernatant are then separated (usually by centrifugation or filtration) and the supernatant is kept for further use.

In the second type of precipitation, the components of interest from a complex solution are selectively precipitated. The precipitate and supernatant are separated (again by centrifugation or filtration) and the precipitate is kept for further use. This precipitate may well be redissolved for further use.

Examples of precipitation that are of particular relevance to this invention will now be discussed.

a. Alcohol Precipitation of Nucleic Acid Molecules from Solution:

Alcohol precipitation of nucleic acid molecules from solution is a standard procedure for the concentration and/or purification of these species from complex solutions. Typical methods involve the addition of salt (e.g. 0.1 volumes of 2.5M sodium acetate (pH 5.2)) to a solution containing nucleic acids followed by addition of an alcohol (e.g. 2.5 volumes of ethanol). The nucleic acids then precipitate. The precipitated nucleic acid molecules aggregate (usually with the aid of reduced temperatures; e.g. 5 minutes on dry ice) and are recovered by centrifugation. After removal of the supernatant, the pelleted precipitate is normally redissolved in the required volume of an appropriate buffer. The nucleic acid may be DNA (partially or wholly single or double stranded), RNA (partially or wholly single or double stranded), mixtures of any of the above or a hybrid RNA/DNA species. The salt used may be sodium acetate, sodium chloride, potassium acetate, potassium chloride, ammonium acetate, ammonium chloride, guanidinium thiocyanate, guanidinium isothiocyanate, guanidinium chloride or mixtures of the above. The alcohol used is normally ethanol or isopropanol.

b. Precipitation of Bacteriophage and Other Viruses from Solution:

Precipitation of bacteriophage and other viruses from solution by the addition of solutions containing high concentrations of highly hydratable polymers, such as polyethylene glycol (PEG), and salts, such as sodium chloride, is a standard procedure for the concentration and/or purification of these species from complex solutions. The bacteriophage or other viruses precipitated in this way may be used for nucleic acid extraction, protein extraction, infection of host cells, structural studies or immunological studies. A typical procedure involves the addition of 0.2 volumes of 20% (w/v) PEG in 2.5M sodium chloride to the complex solution known to contain the bacteriophage or other viruses. The bacteriophage or other viruses precipitate. The precipitated particles then aggregate (normally with the aid of incubation at reduced temperatures; e.g. 60 minutes at 4° C.) and are recovered by centrifugation. After removal of the supernatant, the pellet (comprising precipitated particles of bacteriophage or other viruses) is normally redissolved in the required volume of an appropriate buffer. The bacteriophage may be filamentous (e.g. M13) or complex (e.g. lambda). They may infect bacteria, animal or plant cells and they may be DNA-containing or RNA-containing.

c. Removal of Bacterial DNA, Proteins and Membranes from Bacterial Lysates:

Another type of precipitation of interest to Molecular Biologists is used for the removal of bacterial DNA, proteins and membranes from bacterial lysates containing, in addition to the above, RNA and plasmid DNA and/or cosmid DNA and/or bacteriophage DNA. This forms the basis of the alkaline lysis procedure for preparations of low molecular weight DNA. In this procedure, the bacterial cells (e.g. *E. coli*) are lysed by treatment with sodium hydroxide (e.g. 200 mM) and the detergent sodium dodecyl sulphate (SDS) (e.g. 0.3–1.0% (w/v)). Addition of a mixture of either sodium or potassium acetate at low pH (e.g. 0.5 times the volume of lysis buffer of 3M sodium or potassium acetate adjusted to pH 4.8 with acetic acid) leads to the formation of a precipitate containing protein, membrane fragments and the entrapped bacterial DNA. The RNA and low molecular weight DNA species are not entrapped in this precipitate and can be recovered from the supernatant after centrifugation or filtration of the precipitate. The low molecular weight DNA species can be purified and/or concentrated, along with cellular RNA, by subsequent alcohol precipitation from this supernatant as described above. The DNA species extracted by this procedure may be plasmid, cosmid or bacteriophage-derived. The volume of cells lysed can be as little as a few microliters or as large as many liters of bacterial culture.

II. SUMMARY OF THE INVENTION

In one aspect this invention provides a method of treating a solution of a polymer by the use of magnetically attractable beads which do not specifically bind the polymer, comprising the steps of:

suspending the magnetically attractable beads in the solution, precipitating the polymer out of solution whereby it becomes non-specifically associated with the beads, applying a magnetic field to draw down a precipitate of the beads and the associated polymer, and separating the precipitate from a supernatant liquid.

The key to the invention is the use of magnetically attractable beads (hereinafter magnetic beads). The nature of the magnetic beads is not critical, and commercially available beads may be used. The beads typically have an average diameter in the range 1 to 100 μm, and comprise finely divided magnetizable material encapsulated in organic polymer.

Or the organic polymer may be omitted. Beads of magnetic iron oxide are commercially available. Such beads have been successfully used in this invention in sizes ranging from below 1 μm up to 40 μm. Even the larger beads remain in suspension at least for the duration of the precipitation step; their subsequent tendency to settle out assists the magnetic field in drawing down the precipitate.

To improve recovery of precipitated polymers, the beads may be pretreated to reduce any unwanted tendency to bind the polymers permanently. For example, when the polymers are nucleic acids, the beads may be pre-treated with a phosphate solution. This treatment is believed to phosphatize any exposed magnetisable material, and may not be necessary if the magnetisable material is completely encapsulated in inert polymer.

The beads are preferably added to the solution either before, or together with, a reagent used to precipitate the polymer. Alternatively, the beads may be added after the precipitation step, under conditions to cause the pre-existing precipitate to become associated with them.

The starting solution is preferably aqueous. However starting solutions in polar or non-polar organic solvents are envisaged, particularly when the polymer is of synthetic origin.

While the invention is applicable to polymers generally, it is of particular importance in relation to biopolymers. Biopolymers are polymers found in biological systems. The nature of the biopolymer is not critical to the invention. Biopolymers include nucleic acids (DNA and RNA), proteins, polypeptides, polysaccharides, cell membrane material, bacteriophages, virus, and procaryotic and eucaryotic cells.

At the outset, the polymer or biopolymer is present in solution, the term solution being used broadly to cover permanently stable suspensions in which the polymer molecules are not aggregated.

It is a feature of the invention that the magnetic beads do not specifically bind the polymer. By this feature, the present invention is distinguished from many prior techniques which involve providing a coating on the surface of magnetic beads designed to specifically bind the substance to be drawn down out of solution. When the polymer is precipitated out of solution in the presence of the suspended magnetic beads, it becomes non-specifically associated with the beads. When the beads are drawn down by an applied magnetic field, the associated precipitated polymer is drawn down with them. But when in solution, the polymer does not become associated with the beads.

When the solute is of more interest than the solvent, the method may be used either to concentrate an initially dilute solution, or to recover one or more polymers from a mixture of polymers, or for both these purposes in sequence. For a sequence of manipulations, the same beads can conveniently be used. The nature of the liquids used to dissolve or re-dissolve the polymer, and of reagents used to precipitate polymer, are not material to this invention. A skilled reader will have no difficulty in choosing liquids and reagents appropriate to his needs.

In another aspect, the invention provides an automated device for performing this method, which device comprises an automated pipertot and a magnet which may be a permanent magnet or an electromagnet.

IV. DETAILED DESCRIPTION OF THE INVENTION

Figure 1A:
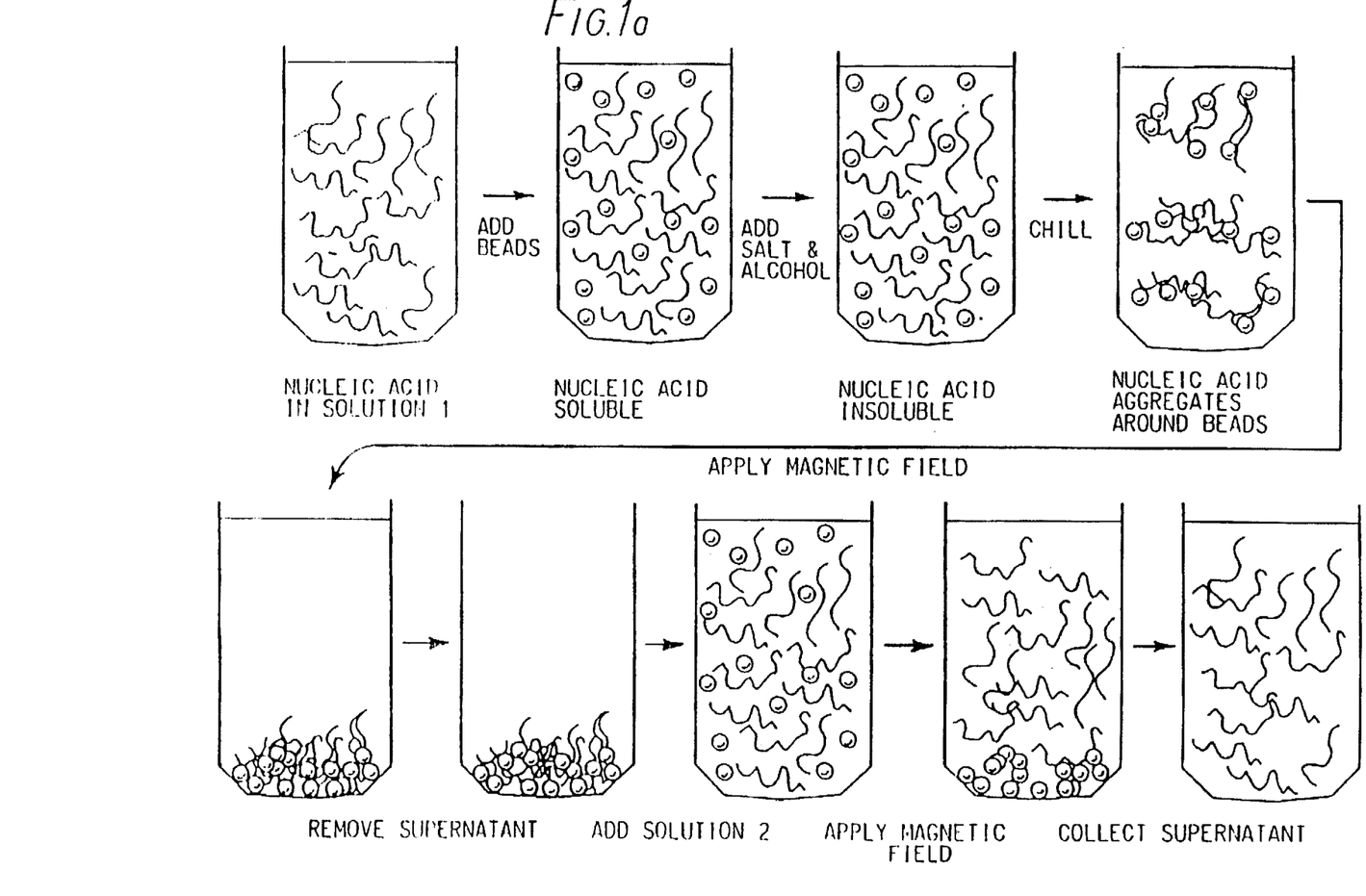
FIG. 1a shows an example of magnetic bead induced separation of nucleic acids with alcohol precipitation in accordance with the present invention.

The invention will now be discussed with reference to the three types of precipitation given in the introduction.

a. Alcohol Precipitation of Nucleic Acid Molecules from Solution:

Magnetic bead induced precipitate separation can be used to greatly improve the process of alcohol precipitation of nucleic acids. The alcohol precipitation procedure as modified by this invention is shown in FIG. 1a. Magnetic beads are added to the nucleic acid in solution. Salt is then added (the magnetic beads can also be added at the same time as the salt). The nucleic acid is still soluble at this stage. Alcohol is then added. This causes the nucleic acid to come out of solution. The precipitated nucleic acid aggregates around the suspended magnetic beads (which may well act as nucleation sites for this aggregation process). The aggregation stage may be assisted for some types of precipitations by chilling (though chilling does not appear to be necessary for simple precautions of plasmid, phage DNA, RNA and genomic DNA by this method). A magnetic field is then applied to the precipitation. This magnetic field is used to draw the complex of magnetic beads and precipitated nucleic acid to the bottom (or side) of the tube. The supernatant is then removed from the tube. At this point, the precipitate can be washed with ethanol, and/or isopropanol and/or 70% (v/v) ethanol to remove any residual salt, nucleotides, chemicals or organic solvents remaining from treatments of the nucleic acid prior to the precipitation step. The nucleic acid is insoluble in isopropanol, ethanol and 70% (v/v) ethanol. The nucleic acid therefore remains aggregated around the magnetic beads during washing. The washing step can thus be performed vigorously (e.g. by vortex mixing) without risk of losing the precipitate. After the washing step, if performed, the precipitate is redissolved in the required volume of an appropriate buffer in the absence of the magnetic field. Reapplication of the magnetic field to the tube results in just the magnetic beads being drawn to the bottom (or side) of the tube (as the nucleic acid is now dissolved rather than a precipitate as before). The redissolved nucleic acid can now be separated from the magnetic beads by collecting the supernatant containing the dissolved nucleic acid with a pipette whilst the beads are held against the bottom (or side) of the tube by the magnetic field.

The modification of alcohol precipitation by this invention has several clear advantages over the conventional method of precipitation using centrifugation. The procedure, as modified by this invention, is:

1. Faster (the modified procedure takes only 1–2 minutes, as opposed to 10–30 minutes for the conventional procedure using centrifugation).

2. Not reliant upon centrifugation equipment.

3. Readily suited to automation (a great many tubes could be placed over a large electromagnet and these could all be alcohol precipitated simultaneously using a multi channel pipetting device).

4. Especially effective if the precipitate of nucleic acid is to be washed with isopropanol, ethanol or 70% ethanol (e.g. to remove any residual salt, nucleotides or organic solvents such as phenol). Washing can be performed rapidly with no risk of loss of material as can occur with the conventional method based upon centrifugation (where the pellet often detaches from the bottom of the tube during such washing).

Figure 1B:
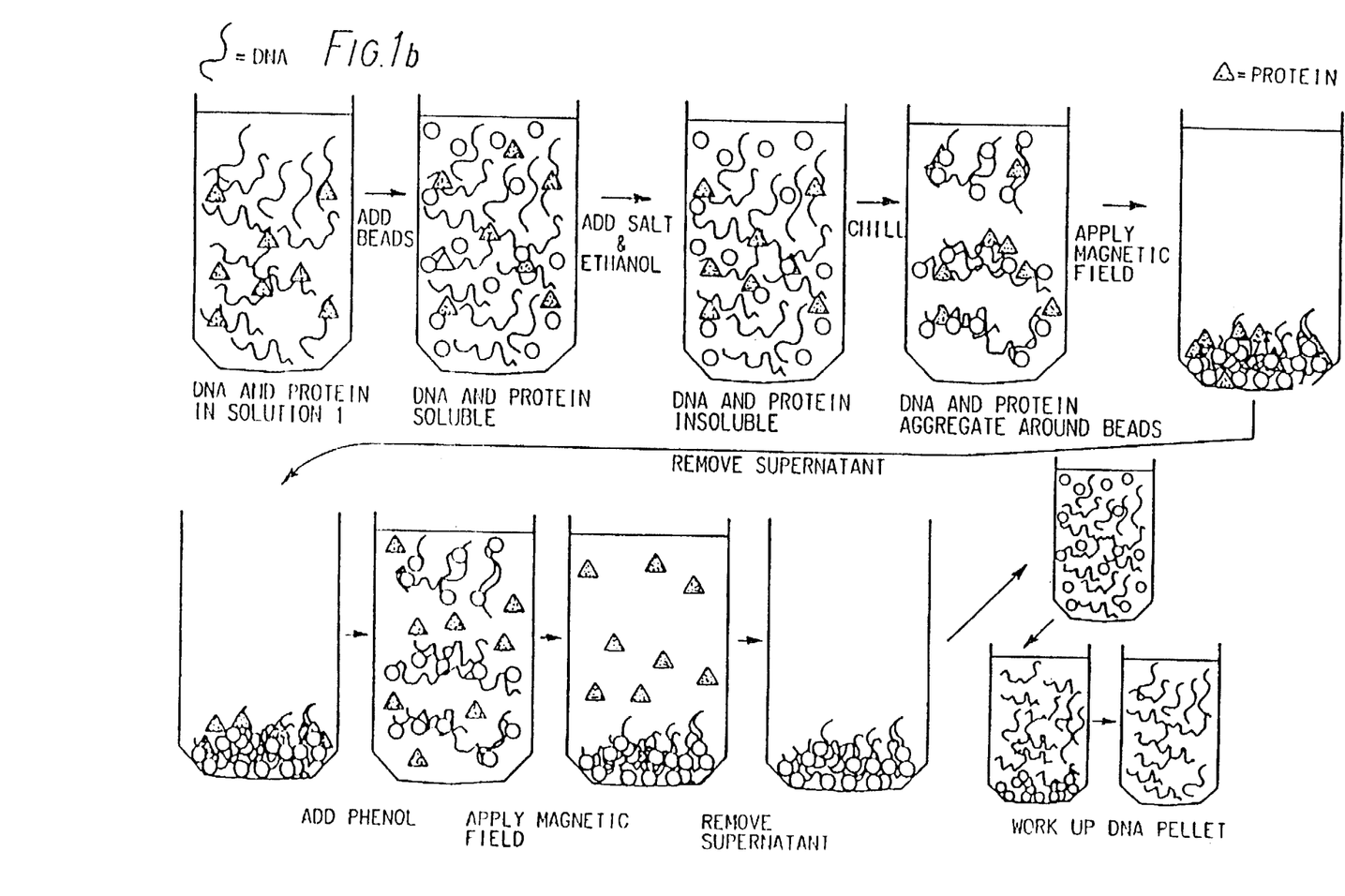
FIG. 1b shows an example of magnetic bead induced precipitate separation of nucleic acids with phenol extraction in accordance with the present invention.

Magnetic bead induced precipitate separation can also be used to greatly improve the process of deproteinization and alcohol precipitation of nucleic acids. The deproteinization and alcohol precipitation procedure as modified by this invention is shown in FIG. 1b. DNA is given as the example in FIG. 4b, though the process is equally applicable to any type of nucleic acid. Magnetic beads are added to the protein and nucleic acid in solution. Salt is then added (the magnetic beads can also be added at the same time as the salt). The protein and nucleic acid are still soluble at this stage. Alcohol is then added. This causes the protein and nucleic acid to come out of solution. The precipitated protein and nucleic acid aggregate around the suspended magnetic beads (which may well act as nucleation sites for this aggregation process). The aggregation stage may be assisted for some types of precipitations by chilling (though chilling does not appear to be necessary for simple precipitations of plasmid, phage DNA, RNA and genomic DNA with protein extraction by this method). A magnetic field is then applied to the precipitation. This magnetic field is used to draw the complex of magnetic beads and precipitated protein and nucleic acid to the bottom (or side) of the tube. The supernatant is then removed from the tube. The protein and nucleic acid remain aggregated around the magnetic beads. Phenol and/or phenol/chloroform and/or phenol/ethanol is then added and the magnetic beads resuspended in the absence of the magnetic field. This resuspension extracts the precipitated protein from the magnetic beads whilst the nucleic acid remains still attached. A magnetic field is again applied to the tube. This magnetic field is used to draw the complex of precipitated nucleic acid and magnetic beads to the bottom (or side) of the tube. The phenolic supernatant (containing the extracted protein) is then removed from the tube. At this point, the precipitate can be washed with ethanol, and/or isopropanol and/or 70% (v/v) ethanol to remove any residual salt, nucleotides, chemicals or organic solvents remaining. The nucleic acid is insoluble in isopropanol, ethanol and 70% (v/v) ethanol. The nucleic acid therefore remains aggregated around the magnetic beads during washing. The washing step can thus be performed vigorously (e.g. by vortex mixing) without risk of losing the precipitate. After the washing step, if performed, the precipitate is redissolved in the required volume of an appropriate buffer in the absence of the magnetic field. Reapplication of the magnetic field to the tube results in just the magnetic beads being drawn to the bottom (or side) of the tube (as the nucleic acid is now dissolved rather than a precipitate as before). The redissolved nucleic acid can now be separated from the magnetic beads by collecting the supernatant containing the dissolved nucleic acid with a pipette whilst the beads are held against the bottom (or side) of the tube by the magnetic field.

The modification of deproteinization and alcohol precipitation by this invention has several clear advantages over the conventional method of using centrifugation. The procedure, as modified by this invention, is:

1. Faster (the modified procedure takes only 5–10 minutes, as opposed to 20–40 minutes for the conventional procedure using centrifugation).

2. Not reliant upon centrifugation equipment.

3. Readily suited to automation (a great many tubes could be placed over a large electromagnet and these could all be deproteinized and alcohol precipitated simultaneously using a multi channel pipetting device).

Figure 2:
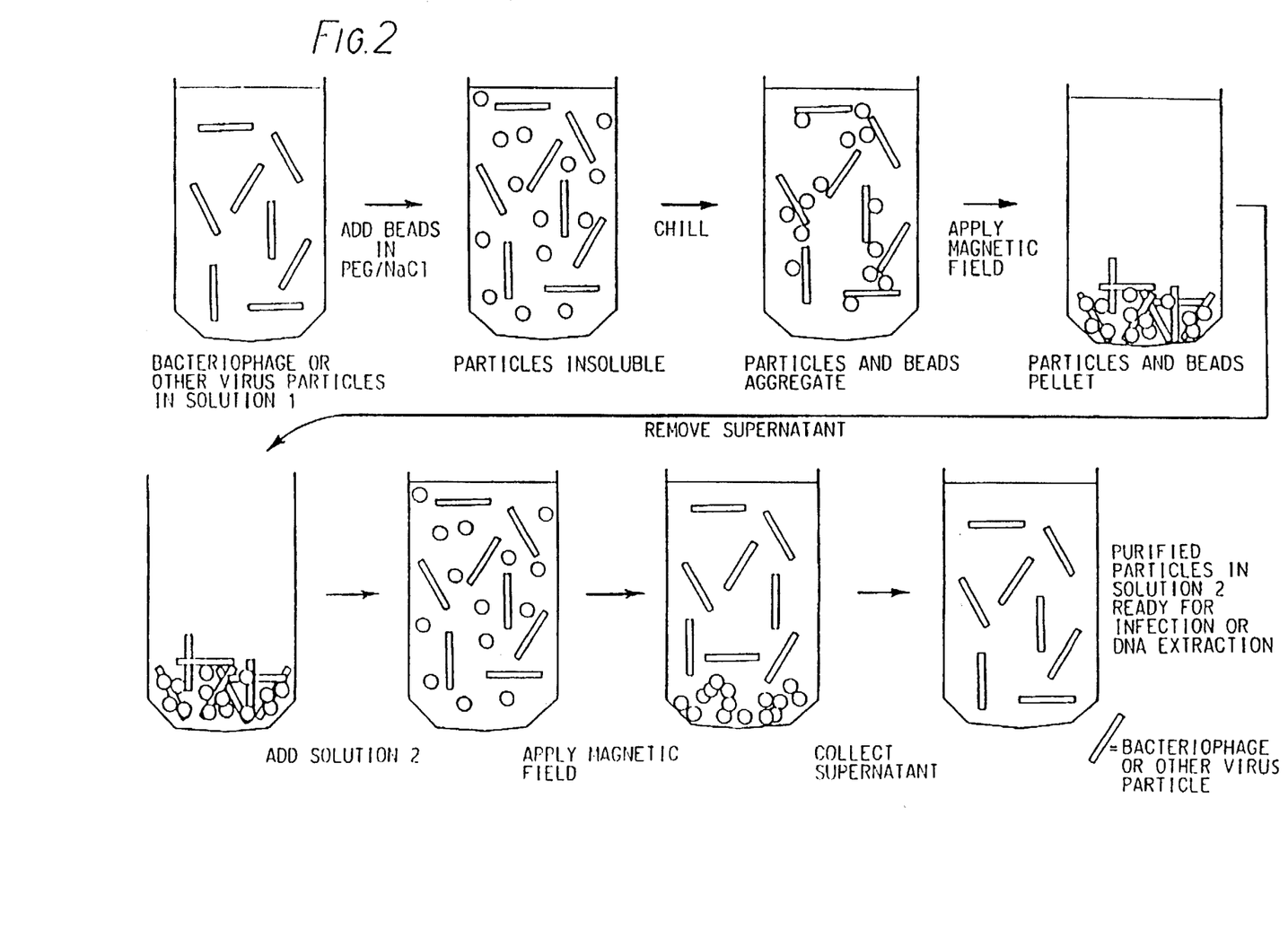
FIG. 2 shows an example of magnetic bead precipitate separation of phage and viruses in accordance with the present invention.

4. Especially effective if the precipitate of nucleic acid is to be washed with isopropanol, ethanol or 70% ethanol (e.g. to remove any residual salt, nucleotides or organic solvents such as phenol). Washing can be performed rapidly with no risk of loss of material as can occur with the conventional method based upon centrifugation (where the pellet often detaches from the bottom of the tube during such washing).

b. Precipitation of Bacteriophage and Other Viruses from Solution:

Magnetic bead induced precipitate separation can be used to greatly improve the process of hydrateable polymer/salt precipitation of bacteriophage and other viruses. The hydrateable polymer/salt precipitation procedure as modified by this invention is shown in FIG. 2. Magnetic beads, hydrateable polymer (e.g. PEG) and salt (e.g. sodium chloride) are added to the bacteriophage or other viral particles in solution. This causes the particles of bacteriophage or other viruses to come out of solution. The precipitated particles aggregate round the suspended magnetic beads (which may well act as nucleation sites for this aggregation process). The aggregation stage may be assisted for some types of precipitations by chilling (though chilling does not appear to be necessary for simple precipitations of bacteriophage). A magnetic field is then applied to the precipitation. This magnetic field is used to draw the complex of magnetic beads and precipitated particles to the bottom (or side) of the tube. The supernatant is then removed from the tube. The precipitate is redissolved in the required volume of an appropriate buffer in the absence of the magnetic field. Reapplication of the magnetic field to the tube results in just the magnetic beads being drawn to the bottom (or side) of the tube (as the particles of bacteriophage or other viruses are now dissolved rather than a precipitate as before). The redissolved particles of bacteriophage or other viruses can not be separated from the magnetic beads by collecting the supernatant containing the dissolved particles with a pipette whilst the beads are held against the bottom (or side) of the tube by the magnetic field.

The modification of hydrateable polymer/salt precipitation by this invention has several clear advantages over the conventional method of precipitation using centrifugation. The procedure, as modified by this invention, is:

1. Faster (the modified procedure takes only 1–2 minutes, as opposed to 65–75 minutes for the conventional procedure using centrifugation).

2. Not reliant upon centrifugation equipment.

3. Readily suited to automation (a great many tubes could be placed over a large electromagnet and these could all be hydrateable polymer/salt precipitated simultaneously using a multi channel pipetting device).

Figure 3:
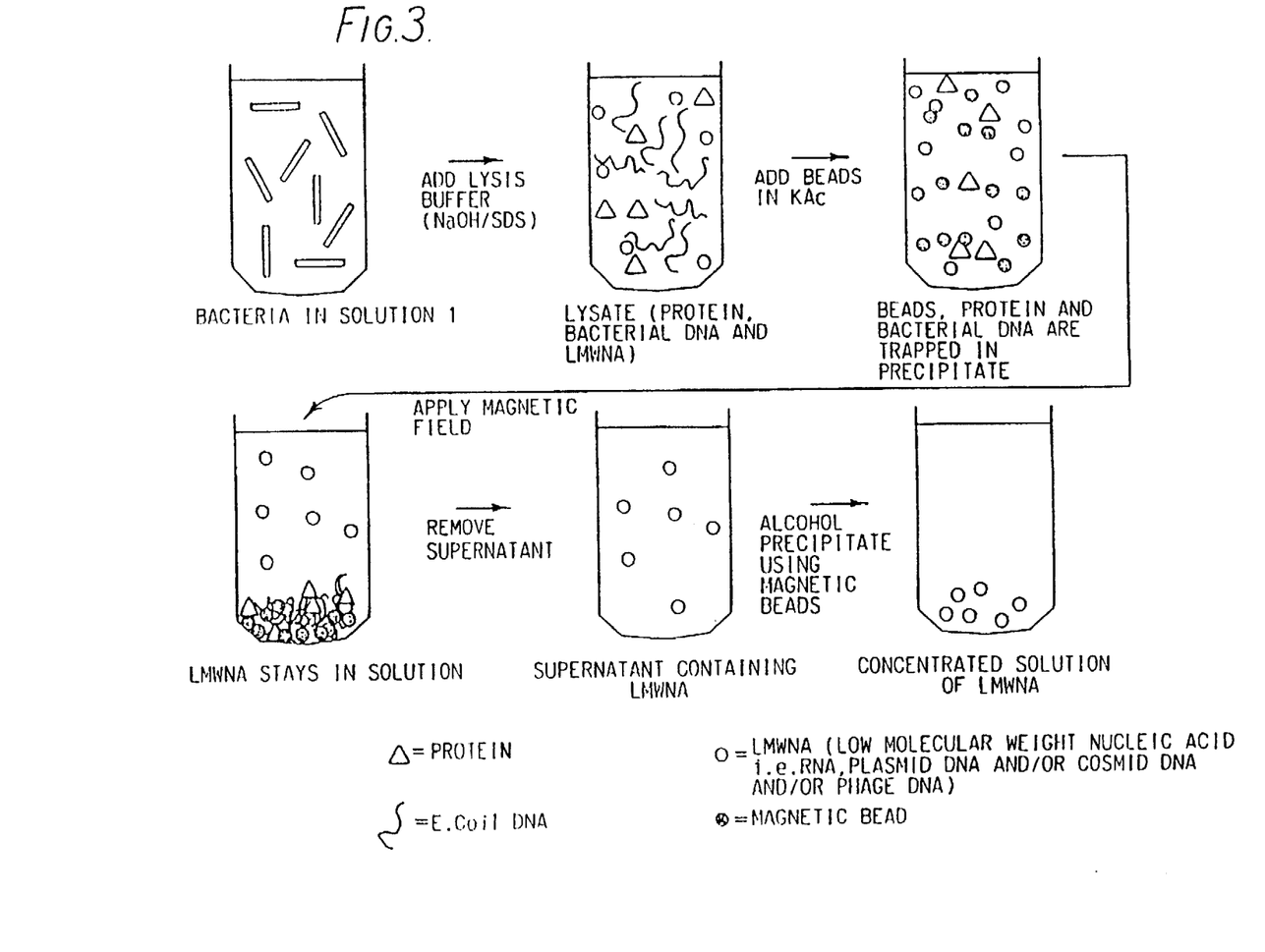
FIG. 3 shows an example of magnetic bead precipitate separation of low molecular weight DNA and RNA in accordance with the present invention.

4. Less likely to produce aerosols of bacteriophage and other viruses than the conventional procedure based upon centrifugation. This is safer if the bacteriophage or other viruses are harmful and will result in less airborne microbial contamination in the laboratory.

c. Removal of Bacterial DNA, Proteins and Membranes from Bacterial Lysates:

Magnetic bead induced precipitate separation can also be used to greatly improve the precipitation of bacterial DNA, membranes and proteins from bacterial lysates containing RNA and low molecular weight DNA species. The preparation of RNA and low molecular weight DNA species as modified by this invention is shown in FIG. 3. Bacteria (containing the low molecular weight DNA species of interest) are lysed with a mixture of sodium hydroxide and SDS. This releases bacterial DNA, proteins, membranes, RNA and low molecular weight DNA into solution. Magnetic beads and either sodium or potassium acetate are then added at low pH. This causes the SDS, proteins and membranes to precipitate. The precipitate also entraps the bacterial DNA and the magnetic beads. A magnetic field is then applied to the precipitation. This magnetic field is used to draw the complex of magnetic beads and precipitated material to the bottom (or side) of the tube. The supernatant is then removed from the tube with a pipette whilst the complex of beads and precipitated material is held against the bottom (or side) of the tube by the magnetic field. The low molecular weight DNA can be purified and/or concentrated from this supernatant (along with any remaining cellular RNA that will also be purified) by alcohol precipitation as described above.

The modification of low molecular weight DNA preparation by this invention has several clear advantages over the conventional method of precipitation using centrifugation. The procedure, as modified by this invention, is:

1. Faster (the modified procedure takes only 5–10 minutes, as opposed to 30–60 minutes for the conventional procedure using centrifugation).

2. Not reliant upon centrifugation equipment.

3. Readily suited to automation (a great many tubes could be placed over a large electromagnet and these could all be precipitated simultaneously using a multi channel pipetting device).

d. DNA Preparation from Bacteriophage or Other Viruses:

Magnetic bead induced precipitate separation has been shown to greatly improve the process of hydrateable polymer/salt precipitation of bacteriophage and other viruses. The hydrateable polymer/salt precipitation has been shown in FIG. 2. Magnetic bead induced precipitate separation has also been shown to greatly improve the precipitation of bacterial DNA, membranes and proteins from bacterial lysates containing RNA and low molecular weight DNA species. The preparation of RNA and low molecular weight DNA species as modified by this invention has been shown in FIG. 3. The combination of these two procedures can be used to derive a novel procedure for the purification of low molecular weight DNA from bacteriophage or other viral particles. In this novel procedure, particles of bacteriophage or other viruses are precipitated using the magnetic bead method given in FIG. 3. The purified particles are then subjected to lysis by sodium hydroxide and SDS. This step separates the coat proteins from the DNA, with both being released into solution. Magnetic beads and either sodium or potassium acetate are then added at low pH. This causes the SDS and coat proteins to precipitate. The precipitate also entraps the magnetic beads. A magnetic field is then applied to the precipitation. This magnetic field is used to draw the complex of magnetic beads and precipitated material to the bottom (or side) of the tube. The supernatant is then removed from the tube with a pipette whilst the complex of beads and precipitated material is held against the bottom (or side) of the tube by the magnetic field. The low molecular weight DNA can be purified and/or concentrated from this supernatant by alcohol precipitation as described above. The modification of low molecular weight DNA preparation from bacteriophage or other viruses by this invention has several clear advantages over the conventional method of precipitation using centrifugation and other methods. The procedure, as modified by this invention, is:

1. Faster (the modified procedure takes only 5–10 minutes, as opposed to 2–3 hours for the conventional procedure using centrifugation).

2. Not reliant upon centrifugation equipment.

3. Readily suited to automation (a great many tubes could be placed over a large electromagnet and these could all be precipitated simultaneously using a multi channel pipetting device).

4. Not reliant upon organic solvent extraction (e.g. by phenol).

5. Less likely to produce aerosols of bacteriophage and other viruses than the conventional procedure based upon centrifugation. This is safer if the bacteriophage or other viruses are harmful and will result in less airborne microbial contamination in the laboratory.

6. Especially effective if the precipitate of nucleic acid is to be washed with isopropanol, ethanol or 70% ethanol. Washing can be performed rapidly with no risk of loss of material as can occur with the conventional method based upon centrifugation (where the pellet often detaches from the bottom of the tube during such washing).

e. Precipitation of Bacteria from Solution

Magnetic bead induced precipitate separation can also be used to effect a novel process of alcohol precipitation of cells e.g. bacterial cells. Magnetic beads are added to the bacteria in solution. Salt is then added (the magnetic beads can also be added at the same time as the salt). The bacteria are still soluble at this stage. Alcohol is then added. This causes the bacteria to come out of solution. The precipitated bacteria aggregate around the suspended magnetic beads (which may well act as nucleation sites for this aggregation process). A magnetic field is then applied to the precipitation. This magnetic field is used to draw the complex of magnetic beads and precipitated bacteria to the bottom (or side) of the tube. The supernatant is then removed from the tube. The precipitate is dissolved in the required volume of an appropriate buffer in the absence of the magnetic field. Reapplication of the magnetic field to the tube results in just the magnetic beads being drawn to the bottom (or side) of the tube (as the bacteria are now dissolved rather than a precipitate as before). The redissolved bacteria can now be separated from the magnetic beads by collecting the supernatant containing the dissolved bacteria with a pipette whilst the beads are held against the bottom (or side) of the tube by the magnetic field.

Alternatively the bacteria can be lysed directly on the beads as described in IIIc for DNA preparation. The procedure as effected by this invention is:

1. Faster (the modified procedure takes only 1–2 minutes, as opposed to 5–15 minutes for the conventional procedure using centrifugation).

2. Not reliant upon centrifugation equipment.

3. Readily suited for automation (a great many culture tubes could be placed over a large electromagnet and these could all be alcohol precipitated simultaneously using a multi channel pipetting device).

V. Reduction of the Invention to Practice

The magnetic beads used were cellulose/ferric oxide (50/50), with a particle size of 1–10 microns diameter. Beads were pretreated by soaking in 100 mM tetrasodium pyrophosphate solution, and stored at 4 degrees in 0.1% (w/v) sodium azide at a concentration of 50 mg/ml.

a. An Example of Alcohol Precipitation of Nucleic Acid Using Magnetic Bead Induced Precipitate Separation:

EXAMPLE 1

Precipitations of plasmid (e.g. pBR322) can be performed according to the following protocol: Take pBR322 DNA in, for example, 100 µl of TE buffer (10 mM Tris-HCl (pH 8.0), 1 mM EDTA (pH 8.0)); add 1/10th volume (i.e. 10 µl) of a solution containing magnetic beads at 50 mg/ml and tRNA at 1 mg/ml (as carrier, this may be omitted if the concentration of nucleic acid is greater than about 10–25 µg/ml) in 2.5M sodium acetate adjusted to pH 5.2 with acetic acid; mix; add 2.5 volumes (i.e. 250 µl) of ethanol; mix; place over a permanent magnet to bring down the precipitate;

remove the supernatant; wash the pellet in, for example, 100 μl of 70% (v/v) ethanol by resuspending with a pipette in the absence of the magnetic field, finally removing the supernatant (wash solution) with a pipette in the presence of the magnetic field; redissolve the pellet in the required volume of TE buffer.

No loss occurs on omission of the chilling step for pBR322 DNA. Also, no loss occurs from washing the precipitate with 70% (v/v) ethanol for pBR322 DNA. The above procedure works equally well for human genomic DNA and for RNA.

EXAMPLE 2

Precipitation of pBR322 plasmid DNA with deproteinization can be performed according to the following protocol: Take, for example, pBR322 DNA in 20 μl of TE buffer (10 mM Tris-HCl (pH 8.0), 1 mM EDTA (pH 8.0)) containing protein (e.g. a ¼ dilution of Rainbow Markers™ (Amersham International)); add 1/10th volume (i.e. 2 μl) of a solution containing magnetic beads at 50 mg/ml and tRNA at 1 mg/ml (as carrier, this may be omitted if the concentration of nucleic acid is greater than about 10–25 μg/ml) in 2.5M sodium acetate adjusted to pH 5.2 with acetic acid; mix; add 2.5 volumes (i.e. 50 μl) of ethanol; mix; place over a permanent magnet to bring down the precipitate; remove the supernatant; wash the pellet in, for example, 50 μl of phenol (or greater than 60% (v/v) phenol in ethanol) by resuspending with a pipette in the absence of the magnetic field, finally removing the supernatant (wash solution) with a pipette in the presence of the magnetic field; redissolve the pellet in the required volume of TE buffer. The yield of DNA falls off with less than 40% (v/v) phenol in ethanol used for protein extraction. No losses are incurred with this additional step of protein extraction compared to a protein-free ethanol precipitation. Ethanol precipitation from a solution heavily contaminated with protein is also seen to be dependent upon the extraction of the contaminating protein by a phenol containing solution (i.e. the DNA cannot be redissolved from the beads if protein extraction has not been performed). The successful extraction of the protein into the phenolic layer by this procedure can clearly be seen when using coloured proteins. The above procedure works equally well for human genomic DNA and for RNA.

b. An Example of Hydrateable Polymer/Salt Precipitation of Bacteriophage Using Magnetic Bead Induced Precipitate Separation:

EXAMPLE 3

Precipitations can be performed on, for example, 1 ml samples of M13mp8 bacteriophage in 2xTY broth (precleared of bacteria by centrifugation) according to the following protocol: Add 0.4 volumes (i.e. 400 μl) of 2 mg/ml magnetic beads in 20% (w/v) PEG, 2.5M NaCl; mix; bring down magnetic beads and precipitate using a permanent magnet; redissolve magnetic bead pellet in the required volume of TE buffer.

At 0.4 volumes, the amount of bacteriophage not brought down by the beads is negligible.

EXAMPLE 4

DNA preparations can be performed on, for example, 1 ml samples of M13mp8 bacteriophage in 2xTY broth (precleared of bacteria by centrifugation) according to the following protocol: Add 0.4 volumes (i.e. 400 μl) of 2 mg/ml magnetic beads in 20% (w/v) PEG, 2.5M NaCl; mix; bring down magnetic beads and precipitate using a permanent magnet; redissolve magnetic bead pellet in 1/5th volume (i.e. 200 μl) of TE buffer; extract with an equal volume (i.e. 200 μl) of phenol; remove aqueous (top) layer; add 1/10th volume (i.e. 20 μl) of a solution containing magnetic beads at 50 mg/ml and tRNA at 1 mg/ml (as carrier, this may be omitted if the concentration of nucleic acid is greater than about 10–25 μg/ml) in 2.5M sodium acetate adjusted to pH 5.2 with acetic acid; mix; add 2.5 volumes (i.e. 500 μl) of ethanol; mix; place over a permanent magnet to bring down the precipitate; remove the supernatant; wash the pellet in, for example, 100 μl of 70% (v/v) ethanol by resuspending with a pipette in the absence of the magnetic field, finally removing the supernatant (wash solution) with a pipette in the presence of the magnetic field; redissolve DNA in the required volume of TE buffer.

EXAMPLE 5

DNA preparations can also be performed on, for example, 1 ml samples of M13mp8 bacteriophage in 2xTY broth (precleared of bacteria by centrifugation) according to the following protocol: Add 0.4 volumes (i.e. 400 μl) of 2 mg/ml magnetic beads in 20% (w/v) PEG, 2.5M NaCl; mix; bring down magnetic beads and precipitate using a permanent magnet; redissolve magnetic bead pellet in 1/10th original volume (i.e. 100 μl) of 4M sodium perchlorate in TE buffer; now add 2.5 volumes (i.e. 250 μl) of ethanol; mix; place over a permanent magnet to bring down the precipitate; remove the supernatant; wash the pellet twice in, for example, 100 μl of 70% (v/v) ethanol by resuspending with a pipette in the absence of the magnetic field, finally removing the supernatant (wash solution) with a pipette in the presence of the magnetic field; redissolve DNA in the required volume of TE buffer.

c. An Example of the Removal of Bacterial DNA, Proteins and Membranes from Bacterial Lysates Using Magnetic Bead Induced Precipitate Separation:

EXAMPLE 6 pUC19 DNA can be extracted from *E. coli* MC1061 cells by the following protocol: Take, for example, 250 μl of bacterial culture; add 1/5th volume (i.e. 50 μl) of 1.2M NaOH, 1.2% (w/v) SDS; mix; incubate 2 minutes at room temperature; now add 3/5th volume (i.e. 150 μl) of 10 mg/ml magnetic beads in 3M potassium acetate adjusted to pH 4.8 with acetic acid; mix; bring down precipitated material with a permanent magnet and keep supernatant; isopropanol precipitate the supernatant as follows: add 1/10th supernatant volume (i.e. 45 μl) of a solution containing magnetic beads at 50 mg/ml and tRNA at 1 mg/ml (as carrier, this may be omitted if the concentration of nucleic acid is greater than about 10–25 μg/ml) in 2.5M sodium acetate adjusted to pH 5.2 with acetic acid; mix; add 0.6 supernatant volumes (i.e. 270 μl) of isopropanol; mix; place over a permanent magnet to bring down the precipitate; remove the supernatant; wash the pellet in, for example, 100 μl of 70% (v/v) ethanol by resuspending with a pipette in the absence of the magnetic field, finally removing the supernatant (wash solution) with a pipette in the presence of the magnetic field; redissolve DNA in the required volume of TE buffer. Preparations can be incubated with 10 μg/ml ribonuclease A for 10 minutes at 37° C. before analysis.

EXAMPLE 7 pUC19 DNA can also be extracted from *E. coli* MC1061 cells by the following protocol: Take, for example, 500 μl of bacterial culture; add 1 volume (i.e. 500 µl) of a solution containing magnetic beads at 5 mg/ml in 0.2M sodium acetate (adjusted to pH 5.2 with acetic acid) dissolved in ethanol; mix; bring down precipitated bacteria with a permanent magnet; remove supernatant and discard; redissolve bacterial pellet in, for example, 300 µl of 0.2M NaOH, 0.2% (w/v) SDS; mix; incubate 2 minutes at room temperature; now add ½ volume (i.e. 150 µl) of 3M potassium acetate adjusted to pH 4.8 with acetic acid; mix; bring down precipitated material with a permanent magnet and keep supernatant; isopropanol precipitate the supernatant as follows: add ⅒th supernatant volume (i.e. 45 µl) of a solution containing magnetic beads at 50 mg/ml and tRNA at 1 mg/ml (as carrier, this may be omitted if the concentration of nucleic acid is greater than about 10–25 µg/ml) in 2.5M sodium acetate adjusted to pH 5.2 with acetic acid; mix; add 0.6 supernatant volumes (i.e. 270 µl) of isopropanol; mix; place over a permanent magnet to bring down the precipitate; remove the supernatant; wash the pellet in, for example, 100 µl of 70% (v/v) ethanol by resuspending with a pipette in the absence of the magnetic field, finally removing the supernatant (wash solution) with a pipette in the presence of the magnetic field; redissolve DNA in the required volume of TE buffer. Preparations can be incubated with 10 µg/ml ribonuclease A for 10 minutes at 37° C. before analysis.

d. An Example of DNA Extraction from Bacteriophage Using Magnetic Bead Induced Precipitate Separation for: Hydrateable Polymer/Salt Precipitation, Removal of Coat Proteins and Alcohol Precipitation of the DNA:

EXAMPLE 8

M13mp8 phage can be precipitated with magnetic beads, PEG and NaCl as described in IIIb. DNA can then be prepared by the alkaline lysis procedure as described in IIIc (dissolving the PEG/NaCl/magnetic beads precipitate of bacteriophage particles in, for example, 250 µl of TE buffer for alkaline lysis). The alkaline lysis method gives M13mp8 DNA at about half the yield of the phenol extraction preparation.

VI. Other Types of Precipitation

These include the following:

Precipitations of bacteria, tissue culture cells and blood cells by suitable precipitants (e.g. an equal volume of ethanolic 0.2M sodium acetate adjusted to pH 5.2 with acetic acid for *E. coli*) and magnetic bead induced precipitate separation.

Ammonium sulphate precipitation of proteins with magnetic bead induced precipitate separation.

Precipitation of proteins by salts other than ammonium sulphate and magnetic bead induced precipitate separation (e.g. sodium perchlorate, sodium iodide, guanidinium chloride, guanidinium thiocyanate, guanidinium isothiocyanate and other chaotropic agents).

Precipitation of proteins by denaturants and magnetic bead induced precipitate separation.

Precipitation of proteins by detergents and magnetic bead induced precipitate separation.

Precipitation of nucleic acids by the detergent cetyl trimethyl ammonium bromide and magnetic bead induced precipitate separation.

Precipitation or proteins and/or nucleic acids with agents such as trichloroacetic acid (that denature due to extremes of pH) and magnetic bead induced precipitate separation.

Selective RNA precipitations from lithium chloride and magnetic bead induced precipitate separation.

Selective precipitations of nucleic acids from other nucleic acids (e.g. precipitations of high molecular weight DNA from oligodeoxyribonucleotides and/or deoxynucleotide polyphosphates) which may work better using magnetic bead induced precipitate separation than centrifugation.

Immune precipitations and magnetic bead induced precipitate separation.

Complement fixation precipitations and magnetic bead induced precipitate separation.

Blood clotting precipitations and magnetic bead induced precipitate separation.

Latex bead precipitation assays and magnetic bead induced precipitate separation.

Haemagluttination assays and magnetic bead induced precipitate separation.

I claim:

1. A method of making a product solution containing a nucleic acid by treating a starting solution containing the nucleic acid by the use of suspended magnetically attractable beads which do not specifically bind the nucleic acid, comprising the steps of:

precipitating the nucleic acid out of the starting solution in the presence of the suspended magnetically attractable beads whereby a nucleic acid precipitate becomes non-specifically associated with the beads, applying a magnetic field to draw down the precipitate of the nucleic acid and the associated beads and to form a first supernatant liquid, separating the precipitate and the associated beads from the first supernatant liquid, adding a liquid to the precipitate and the associated beads to re-dissolve the nucleic acid and re-suspend the beads, applying a magnetic field to draw down the beads and to form a second supernatant liquid, and separating from the beads the second supernatant liquid as said product solution containing the nucleic acid.

2. The method as claimed in claim 1, wherein all of the beads have been pre-treated with a phosphate solution to reduce the tendency of the beads to bind to a nucleic acid.

3. A method of making a product solution containing low molecular weight nucleic acid by treating a starting bacterial lysate containing low molecular weight nucleic acid by the use of suspended magnetically attractable beads which do not specifically bind the nucleic acid, comprising the steps of:

forming in the bacterial lysate a first precipitate selected from the group consisting of cell debris, protein and chromosomal DNA, in the presence of first suspended magnetically attractable beads, which first precipitate becomes non-specifically associated with the first beads, applying a magnetic field to draw down the first precipitate and the associated first beads and to form a supernatant starting solution containing the low molecular weight nucleic acid, recovering the starting solution containing the low molecular weight nucleic acid from the first precipitate and the associated first beads, precipitating the low molecular weight nucleic acid out of the starting solution in the presence of second suspended magnetically attractable beads whereby a low molecular weight nucleic acid precipitate becomes non-specifically associated with the second beads, applying a magnetic field to draw down the low molecular weight nucleic acid precipitate and the second associated beads and to form a first supernatant liquid, separating the low molecular weight nucleic acid precipitate and the associated second beads from the first supernatant liquid, adding a liquid to the low molecular weight nucleic acid precipitate to re-dissolve the nucleic acid and re-suspend the second beads, applying a magnetic field to draw down the second beads, and separating from the second beads a second supernatant liquid as said product solution containing the low molecular weight nucleic acid.

4. The method as claimed in claim 3, wherein all of the beads have been pre-treated with a phosphate solution to reduce the tendency of the beads to bind to a nucleic acid.

5. A method of making a nucleic acid-containing liquid by treating a solution containing protein and nucleic acid by the use of magnetically attractable beads which do not specifically bind the nucleic acid, comprising the steps of:

forming in the solution a first precipitate comprising protein and nucleic acid in the presence of the suspended magnetically attractable beads which first precipitate becomes non-specifically associated with the beads, applying a magnetic field to draw down the first precipitate and associated beads and to form a first supernatant liquid, separating the first precipitate and associated beads from the first supernatant liquid, adding a first liquid to the first precipitate and associated beads to selectively re-dissolve the protein and re-suspend the beads associated with the nucleic acid, applying a magnetic field to draw down a second precipitate of the nucleic acid and the associated beads and to form a second supernatant liquid containing the protein, separating the second supernatant liquid containing the protein from the second precipitate and associated beads, adding a second liquid to the second precipitate to re-dissolve the nucleic acid and re-suspend the beads, applying a magnetic field to draw down the beads and to form a third supernatant liquid containing the nucleic acid, and separating from the beads the third supernatant nucleic acid-containing liquid.

6. The method as claimed in claim 5, wherein all of the beads have been pre-treated with a phosphate solution to reduce the tendency of the beads to bind to a nucleic acid.

7. A method for recovering nucleic acid from a starting solution of bacteriophage, by the use of magnetically attractable beads which do not specifically bind said bacteriophage, which method comprises the steps:

precipitating said bacteriophage out of the starting solution in the presence of the first suspended magnetically attractable beads whereby the bacteriophage becomes non-specifically associated with the beads;

applying a magnetic field to draw down the precipitate of the bacteriophage and the associated first beads and to form a first supernatant;

separating the bacteriophage precipitate and the associated first beads from the first supernatant;

re-suspending the bacteriophage precipitate and separating the associated first beads from the bacteriophage;

lysing said bacteriophage to form a lysate solution comprising protein and nucleic acid;

precipitating out of the lysate solution the nucleic acid in the presence of second suspended magnetically attractable beads whereby a nucleic acid precipitate becomes non-specifically associated with the second beads;

applying a magnetic field to draw down the nucleic acid precipitate and the associated second beads and to form a second supernatant liquid containing the protein;

separating the nucleic acid precipitate and associated second beads from the second supernatant liquid;

adding a liquid to the nucleic acid precipitate to re-dissolve the nucleic acid and re-suspend the second beads;

applying a magnetic field to draw down the second beads and to form a third supernatant liquid containing the nucleic acid; and separating the third supernatant liquid containing the nucleic acid from the associated second beads.

8. The method as claimed in claim 7, wherein all of the beads have been pre-treated with a phosphate solution to reduce the tendency of the beads to bind to a nucleic acid.

* * * * *

(12) EX PARTE REEXAMINATION CERTIFICATE (6809th)
United States Patent
Reeve (10) Number: US 5,681,946 C1
(45) Certificate Issued: May 12, 2009

(54) PRECIPITATING POLYMERS

(75) Inventor: Michael Alan Reeve, Henley-on-Thames (GB)

(73) Assignee: Amersham International PLC, Buckinghamshire (GB)

Reexamination Request:
No. 90/009,061, Mar. 4, 2008

Reexamination Certificate for:
Patent No.: 5,681,946
Issued: Oct. 28, 1997
Appl. No.: 08/627,097
Filed: Apr. 3, 1996

Related U.S. Application Data

(62) Division of application No. 08/253,212, filed on Jun. 2, 1994, now Pat. No. 5,523,231, which is a continuation of application No. 07/855,036, filed as application No. PCT/GB1991/000212 on Feb. 3, 1991, now abandoned.

(30) Foreign Application Priority Data

Feb. 13, 1990 (GB) .............................................. 9003253

(51) Int. Cl.
*B03C 1/01* (2006.01)
*B03C 1/005* (2006.01)
*C07K 1/30* (2006.01)
*C07K 1/00* (2006.01)
*C07H 1/00* (2006.01)
*C07H 1/06* (2006.01)
*C12N 15/10* (2006.01)
*C12N 1/02* (2006.01)
*C12N 7/02* (2006.01)

(52) U.S. Cl. ..................... 536/25.4; 252/62.54; 435/270
(58) Field of Classification Search ....................... None
See application file for complete search history.

(56) References Cited

PUBLICATIONS

Munro et al., Magnetic Seeding to Aid Recovery of Biological Precipitates, *Biotechnology Letters* 3:297–302, 1981.

Bitton et al., Recovery of Coliphages from Wastewater Effluents and Polluted Lake Water by the Magnetite–Organic Flocculation Method, *Applied and Environmental Microbiology* 41(1):93–96, 1981.

Wallace, Precipitation of Nucleic Acids, *Methods in Enzymology* vol. 152, pp. 41–48, 1987.

Landegren et al., DNA Diagnostics—Molecular Techniques and Automation, *Science* 242:229–237, 1988.

Lund et al., Assessment Of Methods for Covalent Binding of Nucleic Acids to Magnetic Beads, Dynabeads™, and the Characteristics of the Bound Nucleic Acids in Hybridization Reactions, *Nucleic Acid Research* 16(22):10861–10880, 1988.

*Primary Examiner*—Alan Diamond (57) ABSTRACT

A method of recovering a biopolymer from solution involves the use of magnetically attractable beads which do not specifically bind the polymer. The beads are suspended in the solution. Then the polymer is precipitated out of solution and becomes non-specifically associated with the beads. When the beads are magnetically drawn down, the polymer is drawn down with them. The polymer can subsequently be resolubilized and separated from the beads.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–4 is confirmed.

Claims 5–8 were not reexamined.

* * * * *